United States Patent
Salter et al.

(10) Patent No.: US 6,786,475 B2
(45) Date of Patent: Sep. 7, 2004

(54) BUBBLE HUMIDIFIER WITH IMPROVED DIFFUSER AND PRESSURE RELIEF DEVICE

(75) Inventors: Peter W. Salter, Tehachapi, CA (US); James M. Davenport, Fallbrook, CA (US); James N. Curti, Bakersfield, CA (US); Barry Crandall, Bakersfield, CA (US)

(73) Assignee: Salter Labs, Arvin, CA (US)

( * ) Notice: Subject to any disclaimer, the term of this patent is extended or adjusted under 35 U.S.C. 154(b) by 0 days.

(21) Appl. No.: 10/151,696

(22) Filed: May 17, 2002

(65) Prior Publication Data

US 2003/0214056 A1 Nov. 20, 2003

(51) Int. Cl.⁷ .................................................. B01F 3/04
(52) U.S. Cl. ..................... 261/62; 261/65; 261/122.1; 128/203.12
(58) Field of Search .............................. 261/62, 63, 65, 261/74, 122.1; 128/203.12, 203.16

(56) References Cited

U.S. PATENT DOCUMENTS

| 1,333,558 A | * | 3/1920 | Minor |
| 2,584,450 A | * | 2/1952 | Holt et al. |
| 3,756,577 A | * | 9/1973 | Breiling |
| 3,778,038 A | * | 12/1973 | Eversole et al. |
| 3,864,440 A | * | 2/1975 | Giocoechea |
| 6,202,991 B1 | * | 3/2001 | Coniglio et al. |

* cited by examiner

Primary Examiner—Scott Bushey
(74) Attorney, Agent, or Firm—Davis & Bujold, PLLC

(57) ABSTRACT

A bubble humidifier for adding humidity to supplied oxygen. The bubble humidifier has a humidifier base, for containing a quantity of liquid, and a cover for the humidifier base. The bubble humidifier has an oxygen inlet for supplying oxygen to the bubble humidifier and an moisturized oxygen outlet for connection to a moisturized oxygen supply conduit for supplying humidified oxygen to a patient, and the oxygen inlet being connected to a diffuser for diffusing the supplying oxygen within the bubble humidifier. The bubble humidifier has a pressure relief device for relieving excess pressure generated within the bubble humidifier during operation thereof. The bubble humidifier defining a longitudinal axis and the diffuser is arranged to discharge the oxygen from the diffuser substantially at an angle normal to the longitudinal axis of the bubble humidifier to minimize flow of liquid, contained within the humidifier base, from entering the moisturized oxygen outlet during operation of the bubble humidifier.

21 Claims, 6 Drawing Sheets

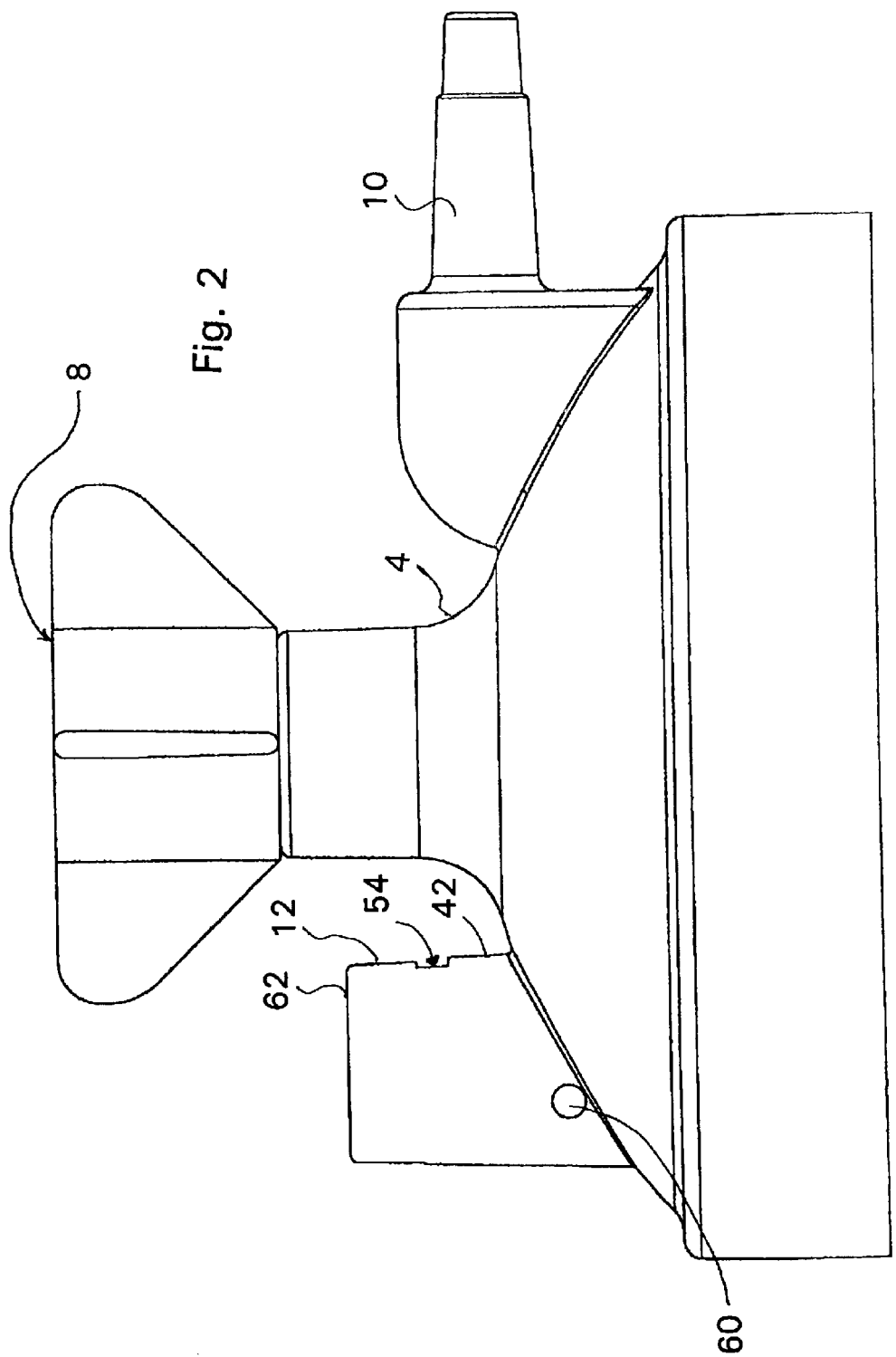

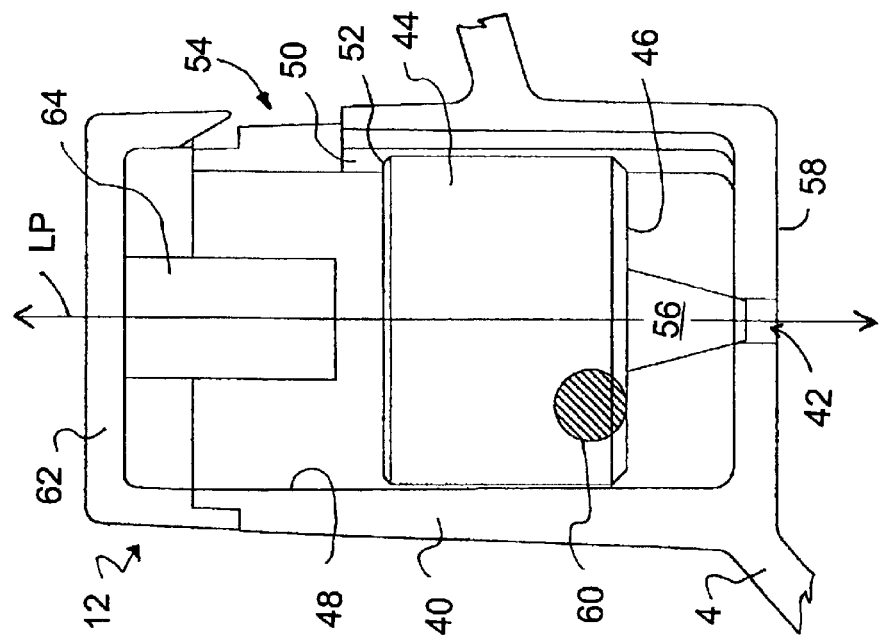
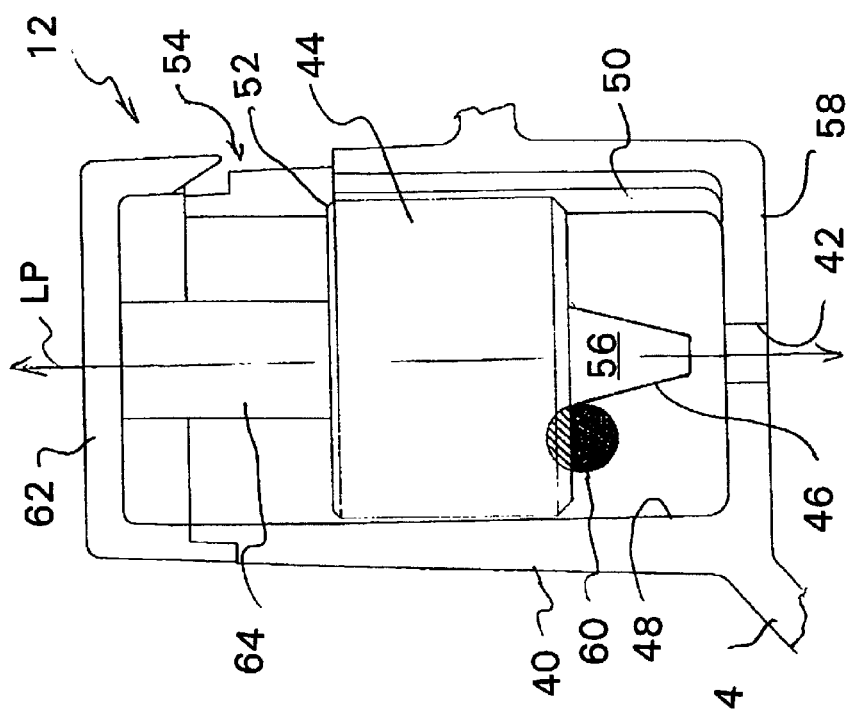

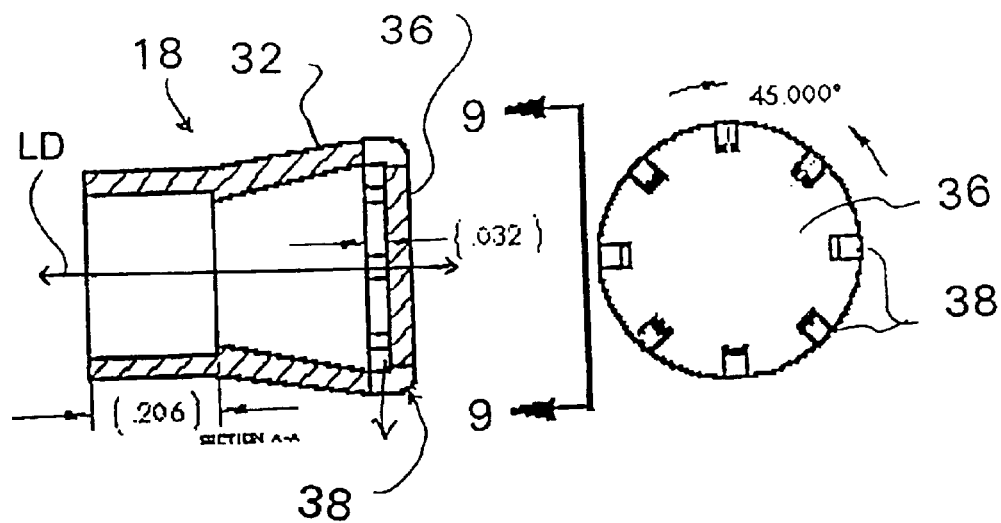
Fig. 8
Fig. 9
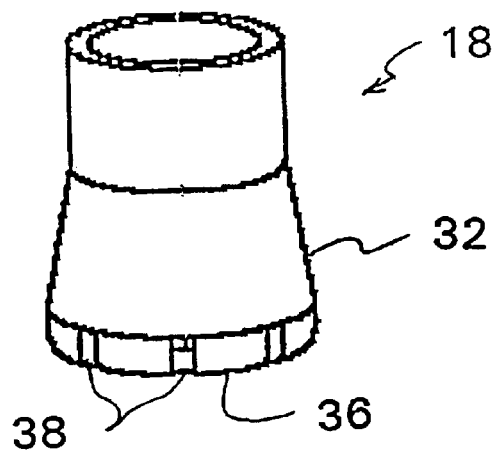
Fig. 10

BUBBLE HUMIDIFIER WITH IMPROVED DIFFUSER AND PRESSURE RELIEF DEVICE

FIELD OF THE INVENTION

The present invention relates to improvements concerning a bubble humidifier used to humidify oxygen prior to dispensing the oxygen to a patient for medical purposes.

BACKGROUND OF THE INVENTION

Oxygen is supplied to patients for a variety of medical reasons. The conventional techniques for generating oxygen typically remove essentially all of the moisture from the generated oxygen so that the oxygen essentially has zero percent relative humidity. Prior to supplying the generated oxygen to a patient, the oxygen is generally sent through a bubble humidifier, or some other humidifying apparatus, where a suitable amount of humidity is added to the oxygen prior to supplying the same to the patient for a medical application.

Standard humidifiers typically operate well for humidifying oxygen at an oxygen flow rate of from about 2 to 4 liters per minute. However, when the flow rate of the supplied oxygen is increased to 6 liters per minute or greater, the currently available bubble humidifiers do not work satisfactorily. In particular, the currently available bubble humidifiers have a tendency to jiggle and shake excessively due to the increase in the oxygen flow rate through the bubble humidifier. Such jiggling or shaking of the bubble humidifier, in turn, has a tendency to cause a valve component of the pressure relief device for the bubble humidifier to become unseated and vent a portion of the moisturized oxygen from the bubble humidifier to the surrounding environment rather than the supplying the same to the patient. Such venting of the supplied oxygen, via the pressure relief device, also causes the pressure relief device to emit a "whistling" sound. This sound generally indicates that at least a portion of the supplied moisturized oxygen is not being conveyed to the patient, e.g., the moisturized oxygen supply conduit for supplying the oxygen to the patient may have a kink therein or is somehow clogged or occluded. In response to the "whistling" sound, the medical personnel will then undertake corrective action, e.g., remove the kink or occlusion from the moisturized oxygen supply conduit.

The conventional pressure relief devices work reasonably well for low oxygen flow rates, e.g., flow rates of 4 liters per minute or less. However, when the flow rate of the oxygen is increased to 6 liters per minute or greater, the conventional pressure relief devices have a tendency to malfunction as the valve of the pressure relief device does not always properly reseat itself to ensure that all of the supplied moisturized oxygen is again conveyed to the patient, via the moisturized oxygen supply conduit, rather than being vented to the surrounding environment The increased oxygen flow rate also has a tendency to cause the oxygen bubbles to coalesce and when the coalescing bubbles filter up through the liquid contained in the bubble humidifier and break the liquid surface. Upon breaking the liquid surface, liquid is splashed and sprayed toward the outlet of the bubble humidifier and into the moisturized oxygen supply conduit. This splashed and sprayed liquid, e.g., water, is then conveyed along with the moisturized oxygen toward a cannula, connected at a remote end of the moisturized oxygen supply conduit, which supplies the moisturized oxygen into the nostrils of a patient. A water trap is installed, along the moisturized oxygen supply conduit, to remove small quantities of liquid from the moisturized oxygen. The conventional water traps work adequately for removing small amounts of water from the moisturized oxygen supply conduit, but the water trap can become quickly clogged if a large quantity of liquid enters the moisturized oxygen supply conduit and is conveyed toward the patient.

SUMMARY OF THE INVENTION

Wherefore, it is an object of the present invention to overcome the above mentioned shortcomings and drawbacks associated with the prior art bubble humidifiers.

Another object of the present invention is to provide a bubble humidifier which is able to add a sufficient amount of moisture to oxygen for a medical application, while minimizing the amount of liquid, e.g., water, which enters into the moisturized oxygen supply conduit exiting from the bubble humidifier.

A further object of the present invention is to provide a pressure relief device which reliably indicates when there is a blockage, kink or some occlusion in the moisturized oxygen supply conduit and also facilitates proper reseating of the valve element once the blockage, kink or occlusion is eliminated from the moisturized oxygen supply conduit.

Yet another object of the present invention is to minimize the amount of liquid that enters into the moisturized oxygen supply conduit and must be removed by a water trap to minimize the associated maintenance required for use of the bubble humidifier.

A still further object of the present invention is to provide a larger bubble humidifier surface area for the bubbles emitted by the diffuser to facilitate a greater and improved dispersion of the oxygen bubbles emitted by the.

Yet another object of the present invention is to minimize the coalescence of the bubbles as they contact the side wall of the container so as to minimize the amount of turbulence of at the surface of the liquid as the oxygen bubbles migrate up through the liquid contained in the bubble humidifier during operation.

The present invention also relates to a bubble humidifier for adding humidity to supplied oxygen, the bubble humidifier comprising: a humidifier base for containing a quantity of liquid; a cover for the humidifier base; the bubble humidifier having an oxygen inlet for supplying oxygen to the bubble humidifier and a moisturized oxygen outlet for connection to a moisturized oxygen supply conduit for supplying humidified oxygen to a patient, and the oxygen inlet being connected to a diffuser for diffusing the supplying oxygen within the bubble humidifier; the bubble humidifier having a pressure relieve device for relieving excess pressure generated within the bubble humidifier during operation thereof; and the bubble humidifier defining a longitudinal axis; wherein the diffuser is arranged to discharge the oxygen from the diffuser substantially at an angle normal to the longitudinal axis of the bubble humidifier to minimize flow of liquid, contained within the humidifier base, from entering the moisturized oxygen outlet and being conveyed along the moisturized oxygen supply conduit during operation of the bubble humidifier.

The present invention also relates to a method of adding humidity to supplied oxygen via the bubble humidifier, the method comprising the steps: providing a humidifier base containing a quantity of liquid; covering the humidifier base with a cover; providing the bubble humidifier with an oxygen inlet for supplying oxygen to the bubble humidifier, connecting an moisturized oxygen outlet to a moisturized oxygen supply conduit for supplying humidified oxygen to a patient, and connecting the oxygen inlet to a diffuser for diffusing the supplying oxygen within the liquid contained by the humidifier base; providing the bubble humidifier with a pressure relieve device for relieving excess pressure generated within the bubble humidifier during operation thereof; defining a longitudinal axis with the bubble humidifier; discharging, via a diffuser, the oxygen from the diffuser substantially at an angle normal to the longitudinal axis of the bubble humidifier to minimize flow of liquid, contained within the humidifier base, from entering the moisturized oxygen outlet and being conveyed along the moisturized oxygen supply conduit during operation of the bubble humidifier.

BRIEF DESCRIPTION OF THE DRAWINGS

The invention will now be described, by way of example, with reference to the accompanying drawings in which:

FIG. 2 is an exploded diagrammatic perspective view of the cover for the bubble humidifier of FIG. 1;

FIG. 3 is a diagrammatic cross-sectional view showing the pressure relief device incorporated within the cover of the bubble humidifier shown in its normally closed position;

FIG. 4 is a diagrammatic cross-sectional view showing the pressure relief device incorporated within the cover of the bubble humidifier shown in its normally opened position with the slug being lifted from its seating engagement with the relief port to remove excess pressure from bubble humidifier;

FIG. 8 is a diagrammatic cross sectional view of the diffuser along section line 8—8 of FIG. 7;

FIG. 9 is a diagrammatic end view of the diffuser 8 along section line 9—9 of FIG. 8; and FIG. 10 is a diagrammatic perspective view of the diffuser of FIG. 6.

DETAILED DESCRIPTION OF THE INVENTION

Figure 1:
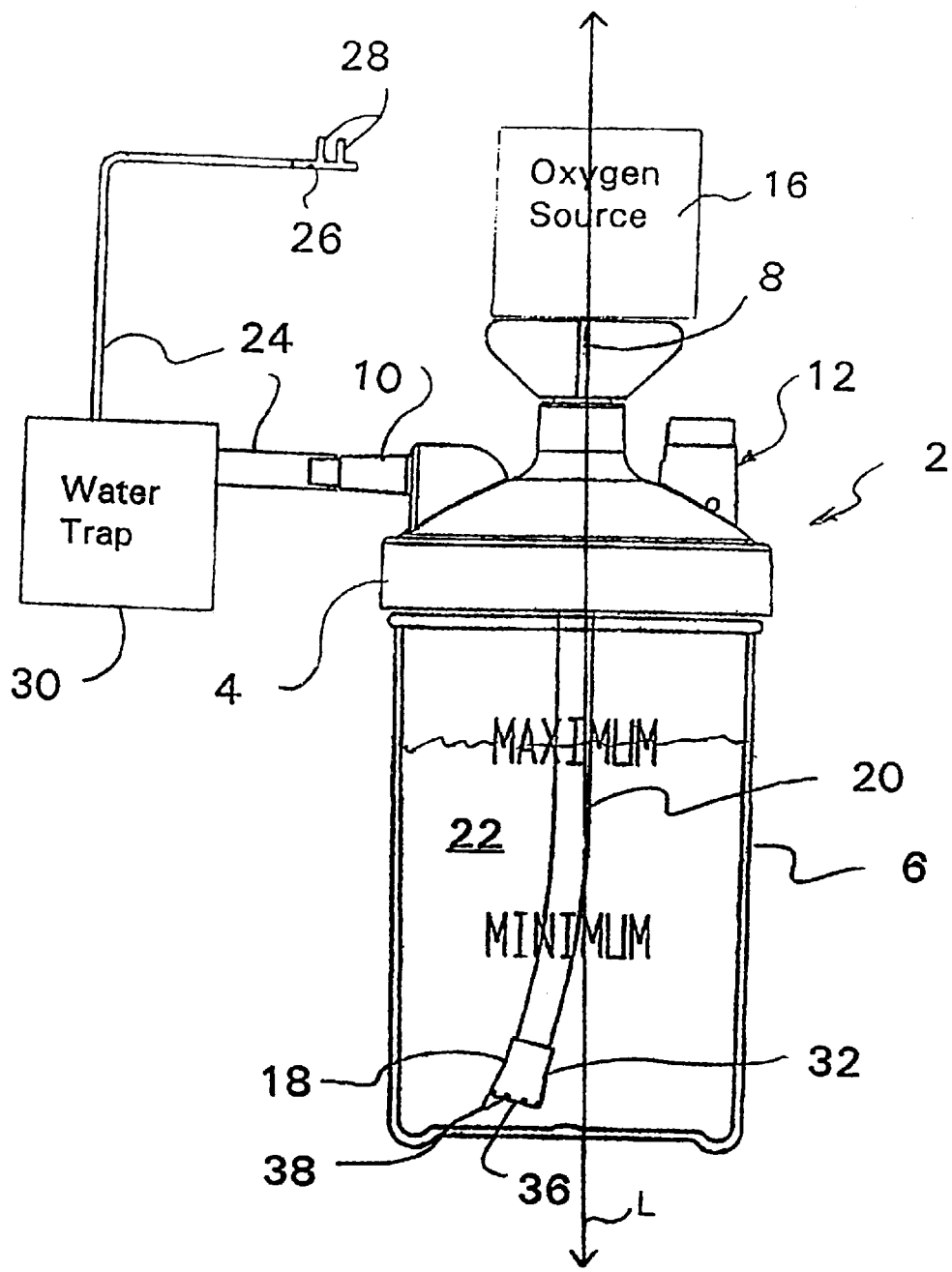
FIG. 1 is a diagrammatic view showing an application for the bubble humidifier of the present invention.

Turning now to FIG. 1, a brief description concerning the basic components of the present invention will now be discussed. As can be seen in this Figure, the bubble humidifier 2 generally comprises a removable cover 4 which sealingly engages with a humidifier base 6 of the bubble humidifier 2 either by a pair of mating screw threads (not shown) carried by the cover 4 and the humidifier base 6 or any other coupling arrangement which is conventional or well known in the art. The humidifier base 6 is designed to hold a sufficient amount of liquid 22, i.e., water. The cover 4 has a centrally located oxygen inlet 8 and an oxygen outlet 10 as well as pressure relief device 12, the function of which will be discussed below in further detail. An outlet of the oxygen generator or source 16 is connected to the oxygen inlet 8 in a conventional manner, e.g., by a threaded wing nut coupling or the like for example. The oxygen source 16 generates a sufficient supply of oxygen and conveys the generated oxygen to the bubble humidifier 2. A diffuser 18 is located within the bubble humidifier 2 and a first end of a humidifier conduit 20 is connected to the oxygen inlet 8, to receive the oxygen conveyed by the flexible oxygen source conduit 14, while a second opposed end of the humidifier conduit 20 is connected to the diffuser 18.

A first end of a moisturized oxygen supply conduit 24 is connected to the oxygen outlet 10 while an opposed second end of the moisturized oxygen supply conduit 24 is connected to an oxygen dispensing device or apparatus, such as a cannula 26. The cannula 26 has a pair of prongs 28 that are generally positioned in the nostrils of the patient to supply the moisturized oxygen to the patient. A conventional water trap 30 is positioned in the moisturized oxygen supply conduit 24, between the oxygen outlet 10 and the cannula 26, to remove any liquid conveyed along with the supplied and moisturized oxygen to the patient.

The important aspect concerning the engagement between the removable cover 4 and the humidifier base 6 is that those two components achieve a substantially gas and water tight seal is therebetween. A conventional oxygen supply system supplies a gas which has an oxygen content of between 93 percent to 95 percent with the balance of the supplied gas being nitrogen and other elements commonly found within air. The humidifier base 6 is typically sized to hold between 100 and 350 cc of liquid 22 to facilitate adding a sufficient amount of humidity to the oxygen being supplied, via the bubble humidifier 2, to the patient.

As can be seen in FIGS. 6–10, the diffuser 18 generally comprises an exterior diffuser housing 32 which has an open first end which is sized and shaped to receive or mate with a remote end of the humidifier conduit 20 conveying the supply of oxygen to the diffuser 18 from the oxygen inlet 8. The remote end of the diffuser housing 32 generally tapers or flares outwardly and is closed or covered by a generally planar end wall or cap 36. The flared end cap 36 and the diffuser 18 may be formed separately from one another or are preferably integral with one another and together define a plurality of peripheral discharge passages 38, e.g., eight discharge passages formed therein. Each one of the discharge passages 38 is equally spaced about the periphery of the diffuser 18, e.g., located at an angle of 45° angle with respect to a longitudinal axis LD defined by the diffuser housing 32. Due to this arrangement, as the oxygen to be moisturized flows along the longitudinal axis LD of the diffuser housing 32, the oxygen impacts against the end cap 36 of the diffuser 18 and is forced and emitted out through one of the discharge passages 38 substantially at a right angle to the longitudinal axis L defined by the bubble humidifier 2. The longitudinal axis LD defined by the diffuser housing 32 is substantially coincident with the longitudinal axis L defined by the bubble humidifier 2. The oxygen emitted out through the discharge passages 38 has a tendency to form oxygen bubbles which are directed at and generally impact against the inner side wall of the humidifier base 6. The oxygen bubbles, emitted out through the discharge passages 38, tend to disperse within the liquid 22 as the oxygen bubbles permeate or filter up through the liquid 22 contained within the humidifier base 6 of the bubble humidifier 2.

The relative high velocity of the oxygen bubbles, emitted out through the discharge passages, is reduced and partially absorbed as the oxygen flows through the liquid 22 toward the side wall of the humidifier base 6. The velocity reduction and energy absorption by the liquid 22 contained within the humidifier base 6 as well as the humidifier base side wall, minimizes the amount of liquid 22 which has a tendency to be splashed or sprayed into the inlet of the moisturized oxygen supply conduit as the moisturized oxygen bubbles permeate upward through the liquid 22 and break the liquid surface.

Figure 5:
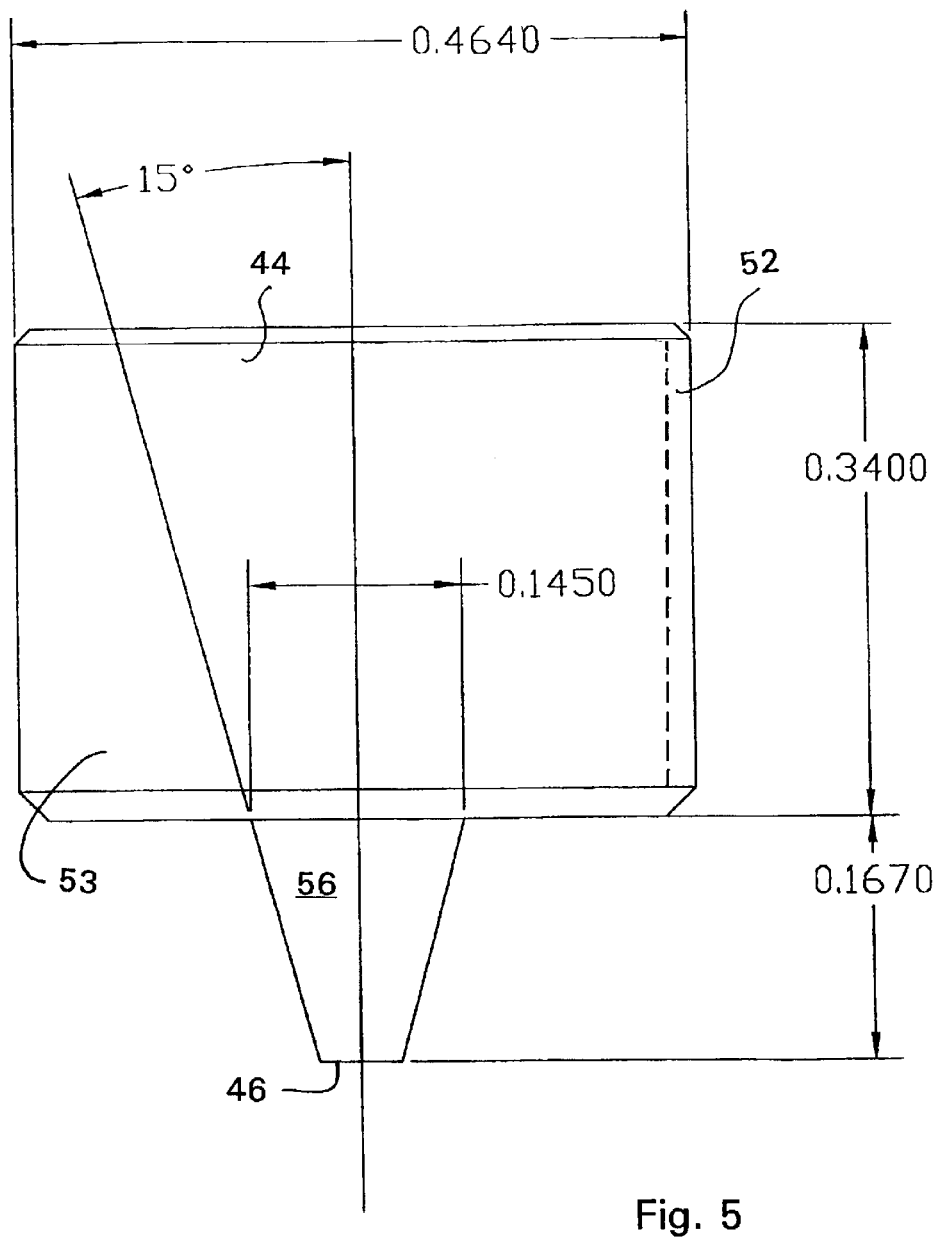
FIG. 5 is a diagrammatic exploded view of the slug incorporated within the pressure relief device of FIG. 3.
Figure 6:
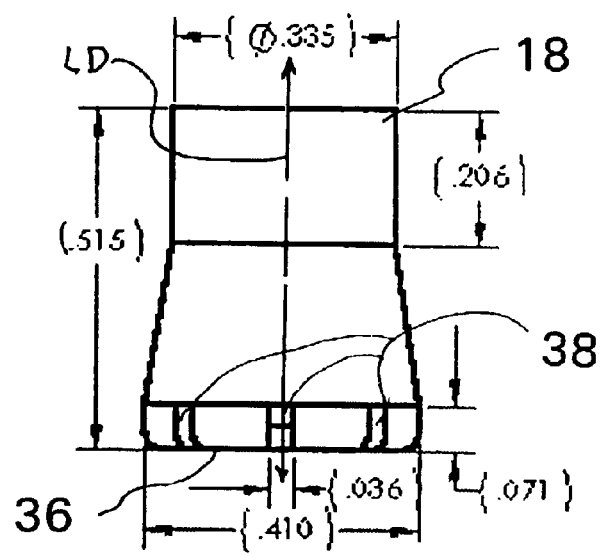
FIG. 6 is a diagrammatic elevational view of the diffuser incorporated within the bubble humidifier for diffusing the oxygen prior to moisturizing the oxygen.
Figure 7:
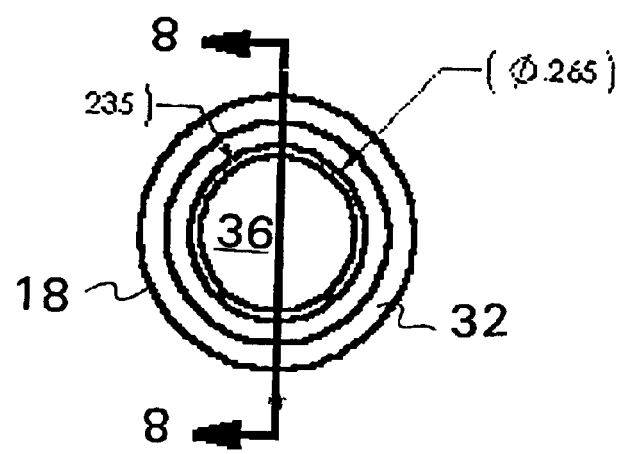
FIG. 7 is a diagrammatic top plan view of the diffuser of FIG. 6.

With reference now to FIGS. 3 through 5, a detailed description concerning the pressure relief device 12 for use with the improved bubble humidifier 2 of the present invention will now be provided. As can be seen in these drawings, the pressure relief device 12 generally comprises a pressure relief housing 40 which has a relief port 42 formed in a base 58 of the pressure relief housing 40 which communicates directly with an interior compartment of the bubble diffuser 2. A movable slug 44 is accommodated within the pressure relief housing 40 and the slug 44 is axially movable along a longitudinal axis LP defined by the pressure relief housing 40. A downwardly facing surface of the slug 44 accommodates a conical shaped valve element 46 and the valve element 46 is sized and shaped to sealingly engage with the relief port 42 provided in the base 58 of the pressure relief housing 40. Due to the weight of the slug 44, e.g. about 8 grams or 0.285 ounces, the valve element 46 normally provides a gas tight seal with the relief port 42 provided in the base 58 of the pressure relief housing 40 to prevent the flow of any oxygen or liquid therethrough.

An inwardly facing surface 48 of the pressure relief housing 40 can be provided with a first guidance member 50, such as an elongate rib which extends substantially along the longitudinal length of the pressure relief housing 40 while a complimentary guidance member 52, e.g., a mating slot, is provided along a side wall 53 of the slug 44. The elongate rib and the mating slot engage with one another to facilitate axial sliding movement of the slug 44 along the longitudinal axis LP of the pressure relief housing 40 while preventing rotation or misalignment of the slug 44 within the pressure relief housing 40. This guidance mechanism 50, 52 also facilitates reseating of the valve element 46 with or over the relief port 42 should the slug 44 be biased away from engagement with the relief port 42 due to the generation of excess pressure within the bubble humidifier 2, and a further detailed description concerning such relief will follow below.

The diameter of the slug 44 is slightly smaller in size than an internal diameter of the pressure relief housing 40 so that, in the event that the valve element 46 of the slug 44 is biased out of engagement with the relief port 42 of the pressure relief housing 40, the oxygen will be allowed to pass between the exterior surface of the slug 44 and the interior surface of the pressure relief housing 40 and exit via an exhaust port 54 formed in the pressure relief housing 40. The exhaust port 54 of the pressure relief device 12 is designed to generate a "whistling" sound, when a gas such as oxygen is exhausted therethrough, to indicate that the pressure relief device 12 is operating. It is to be appreciated that when the pressure relief device 12 is operational, this indicates to the medical personnel that a kink or some sort of blockage or occlusion is contained somewhere along the moisturized oxygen supply conduit 24. When a medical personnel detects a whistling sound emitted by the pressure relief device 12, the medical personnel will carefully examine the moisturized oxygen supply conduit 24 and remove any kink contained therein or remove any occlusion or blockage within the moisturized oxygen supply conduit 24 so that a continuous and uninterrupted supply of humidified oxygen is supplied to the patient.

Once the kink, occlusion or blockage is removed from the moisturized oxygen supply conduit 24, the pressure inside the bubble humidifier 2 will decrease back to a normal operating pressure, e.g., between about 1–3 psi, and the slug 44 will have a tendency to be gradually lowered, by gravity within a few seconds or so, so that the valve element 46 again reseats and seals the relief port 42 of the pressure relief device 12. To ensure that the valve element 46 properly reseats itself each time over the relief port 42 the pressure relief device 12 is activated, the valve element 46 is provided with an inclined conical surface 56 which forms an angle of about 15° with the longitudinal axis LP of the pressure relief device 12. In addition, the valve element 46 has axial length of about 0.167 of an inch and a maximum diameter of about 0.145 of an inch, where the valve element 46 joins with the slug 44. The slug 44 preferably has a diameter of 0.464+/−0.001 of an inch and a height of about 0.34 of an inch. The relief port 42, provided in a base 58 of the pressuring relief device 12, has a diameter of about 0.062 of an inch while the pressure relief housing 40 has an axial length of about 0.49 of an inch.

To facilitate proper reseating of the slug 44 within the relief port 42 provided in the base 58 of the pressure relief device 12, at least one or a pair of opposed side exhaust ports 60 is/are provided in the side wall of the pressure relief housing 40. These side exhaust ports 60 have a diameter of about 0.10 of an inch and are both generally located in the side wall of the pressure relief device 12 at a position so as to communicate with and be covered by a side wall of the slug 44 when the slug 44 in its lowermost position with the valve element 46 sealing engaging with the relief port 42. In the event that the pressure within the bubble humidifier 2 becomes excessive, e.g., in excess of 3 psi for example, the slug 44 will be biased or moved axially away from the base 58 of the pressure relief device 12 whereby the valve element 46 disengages from the relief port 42 provided in the base 58 of the pressure relief device 12. Once this occurs, the side exhaust ports 60 directly communicate with the oxygen entering into the pressure relief device 12, via the relief port 42, and some of this oxygen can be vented through the side exhaust ports 60 directly to the atmosphere while a remainder of the oxygen is vented through the exhaust port 54 and generates the "whistling" sound. The exhaust side ports 60 also facilitate proper reseating of the valve element 46 of the slug 44 with the relief port 42, as soon as the medical personnel removes the kink, occlusion or other blockage contained in the moisturized oxygen supply conduit, since atmospheric air can enter through the side exhaust ports 60. The side exhaust ports 60 thus allow the pressure of the pressure relief device 12 to be quickly equalized and this pressure equalization facilitates proper seating of the valve element 46 with the relief port 42.

A top wall 62 of the pressure relief device 12 is provided with a stop 64 which is located to abut against a rear surface 66 of the slug 44 when the slug 44 is moved to its fully open position. The stop 64 is a generally cylindrical member which is coincident with the longitudinal axis LP of the pressure relief device 12.

The slug 44 is generally designed to relieve the pressure contained within the bubble humidifier 2 once the pressure contained therein is between 3 and 6 psi, for example. The inventors have discovered that conventional pressure relief valves for bubble humidifiers do not operate adequately at higher oxygen flow rates, i.e., oxygen flow rates of between about 6 to about 15 liters per minute or possibly higher. The relief port 42 provided in the base 58 of the pressure relief device 12 is only operational when excessive pressure is generated within the internal compartment of the bubble humidifier 2 and the improved pressure relieve device 12 facilitates more accurate and reliable reseating of the valve element 46 with the relief port 42.

Since certain changes may be made in the above described improved bubble humidifier, diffuser and the pressure relief device, without departing from the spirit and scope of the invention herein involved, it is intended that all of the subject matter of the above description or shown in the accompanying drawings shall be interpreted merely as examples illustrating the inventive concept herein and shall not be construed as limiting the invention.

We claim:

1. A bubble humidifier for adding humidity to supplied oxygen, the bubble humidifier comprising:
   a humidifier base for containing a quantity of liquid;
   a cover for the humidifier base;
   the bubble humidifier having an oxygen inlet for supplying oxygen to the bubble humidifier and a moisturized oxygen outlet for connection to a moisturized oxygen supply conduit for supplying humidified oxygen to a patient, and the oxygen inlet being connected to a diffuser for diffusing the supplied oxygen within the bubble liquid to be contained within the humidifier base;
   the bubble humidifier having a pressure relief device for relieving excess pressure generated within the bubble humidifier during operation thereof; and
   the bubble humidifier defining a longitudinal axis; and the diffuser is arranged to discharge the oxygen from the diffuser at an angle substantially normal to the longitudinal axis of the bubble humidifier to minimize the flow of liquid, to be contained within the humidifier base, from entering the moisturized oxygen outlet and being conveyed along the moisturized oxygen supply conduit during operation of the bubble humidifier;
   wherein at least one side exhaust port is provided in a side wall of the pressure relief device, and the at least one side exhaust port communicates with and is covered by a side wall of a slug when the slug sealing engaging engages with a relief port, and when the excess pressure is generated within the bubble humidifier, the slug is biased axially away from a base of the pressure relief device whereby a valve element of the slug disengages from the relief port and the at least one side exhaust port directly communicates with the oxygen entering into the pressure relief device, via the relief port, and a portion of this oxygen is vented through the at least one side exhaust port directly to atmosphere while a remainder of the oxygen is vented through a second exhaust port.

2. The bubble humidifier according to claim 1, wherein the bubble humidifier is used in combination with an oxygen source and an outlet of the oxygen source is connected with the oxygen inlet of the bubble humidifier; and the moisturized oxygen outlet of the bubble humidifier is connected, via a moisturized oxygen supply conduit, to an oxygen dispensing device for supplying the humidified oxygen to a patient.

3. The bubble humidifier according to claim 2, wherein the oxygen dispensing device is a cannula and a water trap is provided in the moisturized oxygen supply conduit for removing liquid conveyed along with the oxygen to minimize the amount of liquid conveyed to the cannula.

4. The bubble humidifier according to claim 1, wherein a first end of a humidifier conduit is connected to the oxygen inlet, to receive the oxygen conveyed by the oxygen source, while a second opposed end of the humidifier conduit is connected to the diffuser.

5. The bubble humidifier according to claim 1, wherein the cover engages with the humidifier base in a manner such that a substantially gas and water tight seal is achieved between the cover engages and the humidifier base.

6. The bubble humidifier according to claim 1, wherein the humidifier base is sized to hold between 100 and 350 cubic centimeters of the liquid to facilitate adding a sufficient amount of humidity to the oxygen being supplied, via the bubble humidifier, to the patient.

7. The bubble humidifier according to claim 1, wherein the diffuser comprises a diffuser housing and a remote end of the diffuser housing flares outwardly and is closed by an end wall, and a plurality of peripheral discharge passages are formed in the remote end of the diffuser.

8. The bubble humidifier according to claim 7, wherein the plurality of peripheral discharge passages are equally spaced about a periphery of the diffuser and arranged so that the oxygen to be moisturized flows along a longitudinal axis of the diffuser housing, impacts against the end wall and is emitted out through one of the peripheral discharge passages substantially at a right angle to the longitudinal axis defined by the bubble humidifier.

9. The bubble humidifier according to claim 7, wherein the oxygen, emitted out through the plurality of discharge passages, forms oxygen bubbles, and the formed oxygen bubbles disperse within the liquid as the oxygen bubbles permeate and filter up through the liquid contained with in the humidifier base of the bubble humidifier.

10. The bubble humidifier according to claim 1, wherein the pressure relief device comprises a pressure relief housing which has the relief port formed in a base thereof which communicates directly with an interior compartment of the bubble diffuser, and the slug is accommodated within the pressure relief housing, the slug normally seals the relief port but is movable relative to the relief port to relieve the excess pressure generated within the bubble humidifier.

11. The bubble humidifier according to claim 10, wherein the pressure relief device defines a longitudinal axis and the slug is movable along the longitudinal axis defined by the pressure relief device, and a downwardly facing surface of the slug accommodates valve element which is conically shaped to sealingly engage with the relief port.

12. The bubble humidifier according to claim 11, wherein the slug has a weight of about 0.285 ounces, and the valve element normally provides a gas tight seal with the relief port to prevent the flow of any oxygen or liquid therethrough.

13. The bubble humidifier according to claim 1, wherein the pressure relief housing is provided with a first guidance member and the slug has a complimentary guidance member, and the two guidance members facilitate reseating of the valve element over the relief port follow separation of the slug from the relief port.

14. The bubble humidifier according to claim 1, wherein the slug has a diameter which is slightly smaller than an internal diameter of the pressure relief housing so that, in the event that the valve element is biased out of engagement with the relief port, oxygen will be allowed to pass between an exterior surface of the slug and an interior surface of the pressure relief housing and exit via an exhaust port formed in the pressure relief housing.

15. The bubble humidifier according to claim 14, wherein the exhaust port generates a sound, when oxygen is exhausted therethrough, to indicate that the pressure relief device is operating.

16. The bubble humidifier according to claim 11, wherein the valve element has an inclined conical surface which forms an angle of about 15° with the longitudinal axis of the pressure relief device.

17. The bubble humidifier according to claim 11, wherein a top wall of the pressure relief device is provided with a stop which is located to abut against a rear surface of the slug when the slug is moved to a fully open position, and the stop is generally a cylindrical member which is coincident with the longitudinal axis of the pressure relief device.

18. The bubble humidifier according to claim 1, wherein the bubble humidifier operates at an oxygen flow rate of between about 6 to 15 liters per minute.

19. A method of adding humidity to supplied oxygen via the bubble humidifier, the method comprising the steps:
providing a humidifier base containing a quantity of liquid;
covering the humidifier base with a cover;
providing the bubble humidifier with an oxygen inlet for supplying oxygen to the bubble humidifier;
connecting a moisturized oxygen outlet to a moisturized oxygen supply conduit for supplying humidified oxygen to a patient;
connecting the oxygen inlet to a diffuser for diffusing the oxygen within the liquid contained by the humidifier base;
providing the bubble humidifier with a pressure relief device for relieving excess pressure generated within the bubble humidifier during operation thereof;
defining a longitudinal axis with the bubble humidifier;
discharging, via a diffuser, the oxygen from the diffuser substantially at an angle normal to the longitudinal axis of the bubble humidifier to minimize flow of liquid, contained within the humidifier base, from entering the moisturized oxygen outlet and being conveyed along the moisturized oxygen supply conduit during operation of the bubble humidifier;
providing at least one side exhaust port in a side wall of the pressure relief device, and the at least one side exhaust port communicates with and is covered by a side wall of a slug when the slug is sealing engaging with a relief port, and when excess pressure is generated within the bubble humidifier, the slug will be biased axially away from a base of the pressure relief device whereby a valve element disengages from the relief port and the at least one side exhaust port directly communicates with the oxygen entering into the pressure relief device, via the relief port, and a portion of this oxygen is vented through the at least one side exhaust port directly to atmosphere while a remainder of the oxygen is vented through a second exhaust port.

20. A bubble humidifier for adding humidity to supplied oxygen, the bubble humidifier comprising:
a humidifier base for containing a quantity of liquid;
a cover for the humidifier base;
the bubble humidifier having an oxygen inlet for supplying oxygen to the bubble humidifier and a moisturized oxygen outlet for connection to a moisturized oxygen supply conduit for supplying humidified oxygen to a patient, and the oxygen inlet being connected to a diffuser for diffusing the supplied oxygen within the liquid to be contained within the humidifier base;
the bubble humidifier having a pressure relief device for relieving excess pressure generated within the bubble humidifier during operation thereof; and
the bubble humidifier defining a longitudinal axis; and
wherein the diffuser is arranged to discharge the oxygen from the diffuser at an angle substantially normal to the longitudinal axis of the bubble humidifier to minimize the flow of the liquid, to be contained within the humidifier base, from entering the moisturized oxygen outlet and being conveyed along the moisturized oxygen supply conduit during operation of the bubble humidifier, and the diffuser comprises a diffuser housing and a remote end of the diffuser housing flares outwardly and is closed by an end wall, and a plurality of peripheral discharge passages are defined by the end wall and the flared end of the diffuser housing.

21. The bubble humidifier according to claim 20, wherein at least one side exhaust port is provided in a side wall of the pressure relief device, and the at least one side exhaust port communicates with an is covered by a side wall of a slug when the slug sealing engages with a relief port, and when the excess pressure is generated within the bubble humidifier, the slug is biased axially away from the base of the pressure relief device and the excess pressure is at least partially vented via the at least one side exhaust port.

* * * * *